(12) United States Patent
Nguyen et al.

(10) Patent No.: US 11,337,899 B2
(45) Date of Patent: May 24, 2022

(54) COSMETIC COMPOSITION

(71) Applicant: Noxell Corporation, Hunt Valley, MD (US)

(72) Inventors: Ken Nguyen, Randolph, NJ (US); Johanne Richard, Hamburg, NJ (US)

(73) Assignee: Noxell Corporation, Hunt Valley, MD (US)

( * ) Notice: Subject to any disclaimer, the term of this patent is extended or adjusted under 35 U.S.C. 154(b) by 0 days.

(21) Appl. No.: 16/331,933

(22) PCT Filed: Oct. 6, 2017

(86) PCT No.: PCT/US2017/055617
§ 371 (c)(1),
(2) Date: Mar. 8, 2019

(87) PCT Pub. No.: WO2018/067984
PCT Pub. Date: Apr. 12, 2018

(65) Prior Publication Data
US 2019/0240120 A1    Aug. 8, 2019

Related U.S. Application Data

(60) Provisional application No. 62/405,197, filed on Oct. 6, 2016.

(51) Int. Cl.
| | |
|---|---|
| *A61K 8/04* | (2006.01) |
| *A61K 8/25* | (2006.01) |
| *A61K 8/73* | (2006.01) |
| *A61Q 1/02* | (2006.01) |
| *A61K 8/81* | (2006.01) |
| *A61K 8/26* | (2006.01) |
| *A61K 8/37* | (2006.01) |
| *A61P 17/16* | (2006.01) |
| *A61Q 17/04* | (2006.01) |

(52) U.S. Cl.
CPC ............... *A61K 8/042* (2013.01); *A61K 8/25* (2013.01); *A61K 8/26* (2013.01); *A61K 8/375* (2013.01); *A61K 8/73* (2013.01); *A61K 8/731* (2013.01); *A61K 8/8152* (2013.01); *A61P 17/16* (2018.01); *A61Q 1/02* (2013.01); *A61Q 17/04* (2013.01); *A61K 2800/59* (2013.01)

(58) Field of Classification Search
CPC .......... A61Q 1/02; A61Q 17/04; A61K 8/731; A61K 8/25; A61K 8/375; A61K 8/042; A61K 8/73; A61K 8/26; A61K 8/8152; A61K 2800/59; A61P 17/16
See application file for complete search history.

(56) References Cited

U.S. PATENT DOCUMENTS

| | | | |
|---|---|---|---|
| 5,156,911 A | 10/1992 | Stewart | |
| 6,180,122 B1* | 1/2001 | Roulier | ................. A61K 8/042 424/401 |
| 2015/0011641 A1* | 1/2015 | Supamahitorn | ........ A61K 31/14 514/626 |

FOREIGN PATENT DOCUMENTS

| | | |
|---|---|---|
| BR | 112019006470 A2 | 6/2019 |
| CN | 1231166 A | 10/1999 |
| CN | 105163807 A | 12/2015 |
| CN | 105188643 A | 12/2015 |
| CN | 109689013 A | 4/2019 |
| EP | 0951897 | 10/1999 |
| GB | 2363386 A | 12/2001 |
| WO | WO-9965455 A1 | 12/1999 |
| WO | WO-2013093869 A2 | 6/2013 |
| WO | WO-2014128678 A1 | 8/2014 |
| WO | WO-2014128679 A1 | 8/2014 |
| WO | WO-2018067984 A1 | 4/2018 |

OTHER PUBLICATIONS

"International Application Serial No. PCT/US2017/055617, International Search Report dated Dec. 20, 2017", 6 pgs.
"International Application Serial No. PCT/US2017/055617, Written Opinion dated Dec. 20, 2017", 9 pgs.
"International Application Serial No. PCT/US2017/055617, International Preliminary Report on Patentability dated Apr. 18, 2019", 9 pgs.
"European Application Serial No. 17788391.5, Communication Pursuant to Article 94(3) EPC dated Nov. 18, 2020", 4 pgs.
"Chinese Application Serial No. 201780055002.2, Office Action dated Sep. 6, 2021", W/O English Translation, 13 pgs.
"European Application Serial No. 17788391.5, Communication Pursuant to Article 94(3) EPC dated Aug. 6, 2021", 6 pgs.
"Chinese Application Serial No. 201780055002.2, Office Action dated Feb. 15, 2022", with English translation, 26 pages.

\* cited by examiner

*Primary Examiner* — Blessing M Fubara
(74) *Attorney, Agent, or Firm* — Schwegman Lundberg & Woessner, P.A.

(57) ABSTRACT

Provided herein is a cosmetic composition comprising gellant technology combined with at least two different gelling agents; neutralizing agent; colorant; and water.

18 Claims, No Drawings

COSMETIC COMPOSITION

PRIORITY

This application is a U.S. National Stage Filing under 35 U.S.C. 371 from International Application No. PCT/US2017/055617, filed on Oct. 6, 2017, and published as WO 2018/067984 on Apr. 12, 2018, which application claims the benefit of priority from U.S. Provisional Patent Application No. 62/405,197, filed on Oct. 6, 2016, which are herein incorporated in their entirety by reference.

SUMMARY OF THE INVENTION

Provide herein is a gellant technology optionally in combination with colorants and sunscreens to deliver a pigmented cosmetic makeup composition with a novel and unique texture, finish and end benefits.

One embodiment provides a cosmetic composition comprising at least two different gelling agents; colorant; and water. In one embodiment, the composition comprises a lipophilic and a hydrophilic portion, either separate or combined. In another embodiment, the composition further comprises at least one powder, at least one humectant, at least one emulsifier, at least one emollient, at least one film former, at least one sunscreen, at least one preservative, at least one fragrance, at least one antioxidant or a combination thereof.

In one embodiment, the gelling agent comprises between about 0.1 and about 5% by weight of the composition. In one embodiment, at least one gelling agent comprises acrylate copolymer, xanthum gum, biosaccharide gum, clays, hydrophilic silica or a combination thereof. In another embodiment, at least one gelling agent is acrylate/beheneth-25 methacrylate copolymer, Bois Gel, self-emulsifying waxes, oil thickeners, clays, silicas, elastomers or a combination thereof.

In one embodiment, the composition further comprises a neutralizing agent, wherein the neutralizing agent comprises between about 0.1% and about 2.5% by weight of the composition. In one embodiment, the neutralizing agent is sodium hydroxide, citric acid, triethanolamine or a combination thereof.

In one embodiment, the colorant, and optional powder, comprises between about 0.1% to about 25% by weight. In another embodiment, the colorant comprises about 0.1% to about 15% by weight. In one embodiment, the colorant comprises titanium dioxide, iron oxide, mica, dye, organic colorants and pearls, coated or surface treated colorants and powders or a combination thereof. In one embodiment, the powder comprises about 0.5% to about 10% by weight.

In one embodiment, the humectant comprises about 1% to about 15% by weight. In another embodiment, the humectant comprises glycerin, propylene glycol, sodium PCA, galactoarabinan, dipropylene glycol, biosaccharide gum, butylene glycol, pentylene glycol or a combination thereof.

One embodiment provides that the emulsifier comprises about 0.5% to about 8% by weight. In one embodiment, the emulsifier comprises a polymer emulsifier, a polyethylene emulsifier or a combination thereof.

In one embodiment, the emollient comprises about 1% to about 15% by weight. In another embodiment, the emollient comprises nonvolatile silicone, hydrocarbon fluids, caprylic/capric triglyceride, dicaprylyl ether, dimethicone, dimethiconol or combinations thereof. In one embodiment, the emollient comprises caprylic/capric triglyceride, dicaprylyl ether, dimethicone, dimethiconol or combinations thereof.

In one embodiment, the film former comprises about 0.5% to about 5% by weight. In another embodiment, the film former comprises polyurethane-14, acrylates copolymer, galactoarabinan, silicone resin, biosaccharide gum or combinations thereof.

In one embodiment, the sunscreen comprises about 1% to about 30% by weight.

One embodiment provides a method to provide color, make up finish, sunscreen, hydration and long wearing benefits to the skin (e.g., face) of a subject, comprising administering the composition as disclosed herein. Another embodiment provides a method to make a composition comprising a) preparing an aqueous solution in a first container comprising one or more aqueous gellants; once the aqueous solution with aqueous gellant(s) is prepared, colorant(s) (color pigments) are added to the aqueous solution; next, a hydrophilic/lipophilic gellant is added to the aqueous solution; b) an oil phase is prepared in a second container with one or more oils conventionally used in foundation cosmetics, one or more emollients, and an oil-based gellant; and c) the oil phase b) is blended with the aqueous phase a). In one embodiment, the aqueous gellant is xanthan gum and/or carboxy cellulose gums. In one embodiment, xanthan gum is at a concentration range of about 0.1% to about 1% by weight. In one embodiment, the hydrophilic gellant is Net-WRS (a mixture of sorbet-30, tetraisostearate, sorbitan sesquiisostearate, PPG-8 Deteth-20, acrylates/beheneth-25 methacrylate copolymer, dipropylene glycol and water). In another embodiment, the oil based gellant is Bois Gel (a mixture of glyceryl myristate, glyceryl palmitate, glyceryl stearate, glyceryl ricinoleate, glyceryl eicosadioate and dextrin palmitate).

DETAILED DESCRIPTION OF THE INVENTION

Provide herein gellant technology, previously used in non-pigmented skin care products, in combination with other gellants, colorants and sunscreens to deliver a pigmented cosmetic makeup composition providing the end user (e.g., a subject, such as a human) with an assortment of shades via a lightweight texture that applies and leaves a finish which improves the visual appearance of the skin of the face. Also, the pigmented cosmetic product will provide sustainable wear, hydration to the skin and sunscreen protection.

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about"

is used in conjunction with a numerical range, it modifies that range by extending the boundaries above and below the numerical values set forth. In general, the term "about" is used herein to modify a numerical value above and below the stated value by a variance of 20%.

The term "apply" or "application," as used in reference to a composition, means to apply or spread the compositions of the present invention onto keratinous tissue such as the epidermis.

The term "keratinous tissue" refers to keratin-containing layers disposed as the outermost protective covering of mammals (e.g., humans, dogs, cats, etc.) which includes, but is not limited to, skin, lips, hair, toenails, fingernails, cuticles, hooves, etc.

The term "dermatologically acceptable" means that the compositions or components described are suitable for use in contact with human skin tissue without undue toxicity, incompatibility, instability, allergic response, and the like.

The terms "comprises," "comprising," and the like can have the meaning ascribed to them in U.S. Patent Law and can mean "includes," "including" and the like. As used herein. "including" or "includes" or the like means including, without limitation.

Process and Composition:

Provide herein is a gellant technology optionally in combination with colorants and sunscreens to deliver a pigmented cosmetic makeup composition with a novel and unique texture, finish and end benefits.

Provided herein is a gel cream colorant composition with thickening polymer, hydrating and protective properties. The composition comprises an anionic acrylate/beheneth-25 methacrylate copolymer and at least about 40% by weight water. The composition can also comprise any combination of colorant(s) and sunscreen filter(s), powder(s), film former(s), neutralizing agent(s), humectant(s), preservative(s), emollient(s), gellants(s), bioactive(s), chelating agent and/or fragrance(s). This composition delivers a "jelly" texture, lightness and care more associated with non-pigmented skin care products while also delivering the color, wear and finish associated with pigmented cosmetic make up products.

The cosmetic composition of the claimed inventive embodiments is an emulsion that includes two separate gelled phases. One embodiment for making the cosmetic composition includes preparing an aqueous solution that includes a strong gelling and suspending agent, such as xanthan gum, in a concentration within a range of 0.1 to 5 percent by weight, such as a range of 3 to 5 percent by weight. Other gums, such as carboxycellulose gums are suitable for use, within the 0.1 to 5 percent concentration range, such as a range of 3 to 5 percent by weight. Once the aqueous solution with the gellant(s) is prepared, color pigments are added to the aqueous solution. Pigments include those conventionally known in the art, within 0.1-25% total powder concentration. Humectant(s), chelating agent and additional powder(s) may be included in this phase.

Next, in one embodiment, a gellant emulsifier, Net-WRS is added to the formulation. Net-WRS is manufactured by Barnet Products Corp. of Englewood Cliffs. N.J. The Net-WRS is a mixture of sorbeth-30, tetraisostearate, sorbitan sesquiisostearate, PPG-8 Deceth-20, acrylates/beheneth-25 methacrylate copolymer, dipropylene glycol and water. This composition for cosmetic use is a thickening polymeric gel with lipophilic and hydrophilic portions that form a matrix.

An oil phase is prepared with one or more oils conventionally used in foundation cosmetics, one or more emollients including sunscreen filters, and an oil-based gellant, such as Bois Gel, manufactured by Barnet Products Corp. of Englewood Cliffs, N.J. The Bois Gel includes glyceryl myristate, glyceryl palmitate, glyceryl stearate, glyceryl ricinoleate, glyceryl eicosadioate and dextrin palmitate. Other oil based gellants may be used such as, but not limited to, self-emulsifying waxes, oil thickeners, clays, silicas and elastomers.

The oil phase is blended with the aqueous phase then a neutralizer is used to set the desired pH for jellification of the polymeric gel emulsifiers. Film former(s), preservative(s), bioactive(s) and fragrance may be included at this point. The neutralizer can be added at any point of the formation of the water phase or final emulsion.

The addition of the oil phase and aqueous phases will create a final embodiment, comprising a mixture of polymer emulsifier and polyethylene emulsifiers with any combination of water dispersible colorants and powders between 0.1-25%, physical and chemical sunscreen filters between 2-30%, water between 30-90%, including 40-80%, film forming polymers between 0.5-5%, neutralizing agent between 0.1-2.5%, humectants, preservatives, emollients, gellants, bioactives, chelating agent and fragrance.

The water content of the composition can be as low as 30% by weight and may be as high as 90%, including for example 40% to 80%. This insures the hydration, lightness and freshness.

Suitable aqueous gellants include, but are not limited to, acrylate copolymer, xanthum gum, biosaccharide gum, including all aqueous gellants listed in the CTFA Vol. 6, and the mixtures thereof. This provides proper suspending and gelling of aqueous phase.

Suitable humectants include but are not limited to, glycerin, propylene glycol, sodium PCA, galactoarabinan, dipropylene glycol, biosaccharide gum, butylene glycol, pentylene glycol including all humnectants listed in the CTFA Vol. 6, and the mixtures thereof. These contribute to the moisturizing benefits of the composition.

Colorants suitable for this gel product include, but are not limited to, titanium dioxide, iron oxide, mica, dye, organic colorants and pearls with and without coating or surface treatment. These provide the color payoff.

In one embodiment, the bioactives/antioxidants used in the cosmetic composition include, but are not limited to, retinyl palmitate, tocopheryl acetate, ascorbyl palmitate, and other forms of antioxidants. These provide antioxidant activity and other benefits to the skin.

The cosmetic composition of the present invention includes at least one film forming polymer with the objective to increase the wear of the colorants on the skin. According to the invention, the film forming polymer used in the composition includes, but is not limited to polyurethane-14, acrylates copolymer, galactoarabinan, silicone resin, and biosaccharide gum. This is to enhance the wear of the product.

In one embodiment, to avoid the negative effects in the presence of the metallic ions in the composition of the invention, disodium EDTA is used as a sequestering or chelating agent.

Furthermore, in one embodiment, to make the cosmetic composition more presentable, spherical and absorbent powders, including but not limited to, opacifiers and sensory modifiers such as barium sulfate, bismuth oxychloride, boron nitride, and/or kaolin and polymethyl methacrylate including all spherical and absorbent powders listed in the CTFA Vol. 6, may be used in the composition.

In at least one embodiment, the neutralizing agent includes, but is not limited to, sodium hydroxide, citric acid, triethanolamine or mixtures thereof.

Suitable oil based gellants includes but are not limited to, dextrin palmitate, tribehenin, trihydroxystearin, myristic/palmitic/stearic/ricinoleic/eieosanedioic glycerides, polyglyceryl waxes, self-emulsifying waxes, oil thickeners, clays, silica, elastomers, oil absorbent powders.

In one embodiment, the composition comprises one or more emollients, such as any suitable ester including, but not limited to, nonvolatile silicone, and/or hydrocarbon fluids. Emollients can also include caprylic/capric triglyceride, dicaprylyl ether, dimethicone, dimethiconol and mixtures thereof. These contribute to the comfort, film forming and finish of the formulation. Sunscreen filters may also be included in the oil phase, such as organic filters and inorganic filters for sunscreen protection.

The following example is intended to further illustrate certain embodiments of the invention and are not intended to limit the scope of the invention in any way.

EXAMPLE

Example I

| | |
|---|---|
| water | 40-80% |
| humectant | 1-15% |
| gellant | 0.1-5% |
| powder | 0.5-10% |
| colorants | 0.1-15% |
| emulsifier | 0.5-8% |
| emollients | 1-15% |
| sunscreen filters | 1-30% |
| film formers | 0.5-5% |
| neutralizing agent | 0.1-2.5% |
| total | 100% |

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A pigmented cosmetic makeup composition comprising at least two different gelling agents;
   a neutralizing agent, wherein the neutralizing agent comprises between about 0.1% and about 2.5% by weight of the composition, wherein the neutralizing agent is sodium hydroxide, citric acid, triethanolamine or a combination thereof;
   an emollient, wherein the emollient comprises about 1% to about 15% by weight, wherein the emollient comprises nonvolatile silicone, hydrocarbon fluids, caprylic/capric triglyceride, dicaprylyl ether, dimethicone, dimethiconol or combinations thereof;3
   at least one powder that comprises about 0.1% to about 25% by weight;
   colorant; and
   water,
   wherein the pigmented cosmetic makeup composition is an emulsion that includes two gelled phases comprising an aqueous gelled phase and oil gelled phase.

2. The composition of claim 1, wherein the composition comprises a thickening polymeric gel with a lipophilic and a hydrophilic portion that form a matrix.

3. The composition of claim 1, wherein the gelling agent comprises between about 0.1 and about 5% by weight of the composition.

4. The composition of claim 1, wherein at least one gelling agent comprises acrylate copolymer, xanthum gum, biosaccharide gum, clays, hydrophilic silica or a combination thereof.

5. The composition of claim 1, wherein at least one gelling agent is acrylate/beheneth-25 methacrylate copolymer, self-emulsifying waxes, oil thickeners, clays, silicas, elastomers, or a mixture of glyceryl myristate, glyceryl palmitate, glyceryl stearate, glyceryl ricinoleate, glyceryl eicosadioate and dextrin palmitate.

6. The composition of claim 1, wherein the colorant comprises between about 0.1% to about 25% by weight.

7. The composition of claim 1, wherein the colorant comprises about 0.1% to about 15% by weight.

8. The composition of claim 1, wherein the colorant comprises titanium dioxide, iron oxide, mica, dye, organic colorants and pearls, coated or surface treated colorants and powders or a combination thereof.

9. A method to provide color, make up finish, sunscreen, hydration and long wearing benefits to the skin of a subject, comprising administering the composition of claim 1.

10. The composition of claim 1 comprising at least one humectant, at least one emulsifier, at least one emollient, at least one film former, at least one sunscreen, at least one preservative, at least one fragrance, at least one antioxidant or a combination thereof.

11. The composition of claim 10, wherein the powder comprises about 0.5% to about 10% by weight.

12. The composition of claim 10, wherein the humectant comprises about 1% to about 15% by weight.

13. The composition of claim 10, wherein the humectant comprises glycerin, propylene glycol, sodium salt of pyrrolidone carbonic acid (sodium PCA), galactoarabinan, dipropylene glycol, biosaccharide gum, butylene glycol, pentylene glycol or a combination thereof.

14. The composition of claim 10, wherein the emulsifier comprises about 0.5% to about 8% by weight.

15. The composition of claim 10, wherein the emulsifier comprises a polymer emulsifier, a polyethylene emulsifier or a combination thereof.

16. The composition of claim 10, wherein the film former comprises about 0.5% to about 5% by weight.

17. The composition of claim 10, wherein the film former comprises polyurethane-14, acrylates copolymer, galactoarabinan, silicone resin, biosaccharide gum or combinations thereof.

18. The composition of claim 10, wherein the sunscreen comprises about 1% to about 30% by weight.

* * * * *